United States Patent
Devi et al.

(10) Patent No.: US 7,341,855 B2
(45) Date of Patent: Mar. 11, 2008

(54) **PLANT MANGROVE-ASSOCIATED FUNGUS *CURVULARIA LUNATA* AND A SIMPLE AND EFFICIENT METHOD OF OBTAINING HIGH YIELD OF PURE MANNITOL FROM THE SAME**

(75) Inventors: Prabha Devi, Goa (IN); Chandrakant Govind Naik, Goa (IN); Solimabi Wahidulla, Goa (IN); Lisette D'Souza, Goa (IN); Ely Rodrigues, Goa (IN); Asha Peketi, Goa (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/364,029

(22) Filed: Mar. 1, 2006

(65) Prior Publication Data

US 2006/0205050 A1 Sep. 14, 2006

Related U.S. Application Data

(62) Division of application No. 10/464,845, filed on Jun. 19, 2003, now abandoned.

(51) Int. Cl.
*C12P 7/02* (2006.01)
*C12P 7/04* (2006.01)
*C12P 7/14* (2006.01)
*C12P 7/18* (2006.01)

(52) U.S. Cl. .................. 435/155; 435/157; 435/158; 435/162; 435/171

(58) Field of Classification Search .............. 424/93.5; 435/155, 157, 158, 162, 171
See application file for complete search history.

(56) References Cited

U.S. PATENT DOCUMENTS 4,996,149 A 2/1991 Jarreau et al.
5,250,424 A 10/1993 Bills et al.

OTHER PUBLICATIONS

Weymarn et al., "Production of D-Mannitol by Heterofermentative Lactic Acid Bacteria", Process Biochemistry vol. 37:1207-1213, (2002).
Domelsmith et al., "Production of Mannitol By Fungi From Cotton Dust", Applied and Environmental Microbiology, vol. 54(7):1784-1790, (1988).
Yun et al., "A Comparative Study of Mannitol Production by Two Lactic Acid Bacteria", Journal of Fermentation and Bioengineering, vol. 85(2):203-208, (1998).
Yun et al., "Mannitol Accumulation During Fermentation of Kimchi", Journal of Fermentation and Bioengineering, vol. 81(3):279-280, (1996).
Paraszkiewicz et al., "Emulsifier production by steroid transforming filamentous fungus *Curvularia lunata*. Growth and product characteristics", J. of Biotechnology, Jan. 2002 (92) 287-294.
Collins et al., "Biotransformation of cadina-4, 10(15)-dien_3_one and 3-alpha-hydroxycadina-4, 10(5)-diene by *Curvularia lunata* ATCC 12017", Phytochemistry, Mar. 2002 (59) 489-492.

*Primary Examiner*—Ruth A Davis
(74) *Attorney, Agent, or Firm*—Ann S. Hobbs; Venable, LLP

(57) ABSTRACT

The present invention relates to a plant mangrove-associated fungus *Curvularia lunata*, and a simple and efficient method of obtaining high yield of pure mannitol from a plant mangrove-associated fungus *Curvularia lunata*, said method comprising steps of cutting the leaves into small pieces and placing it on potato dextrose agar (PDA) plates for 48 hours, maintaining the culture at temperature ranging between 26-47° C. and salinity ranging between 4-32 ppt with occasional stress conditions for about 17-19 days to obtain mycelial mat, sonicating the mat to lyse the cells, extracting crude from the sonicated mat using methanol repeatedly, concentrating the crude, treating the concentrated crude extract with solvents of increasing polarity, obtaining aqueous fraction as white powder residue after the treatment containing crude mannitol, purifying the crude mannitol by chromatography to obtain pure mannitol with about 75% of the total crude extract.

12 Claims, 1 Drawing Sheet

Figure 1:
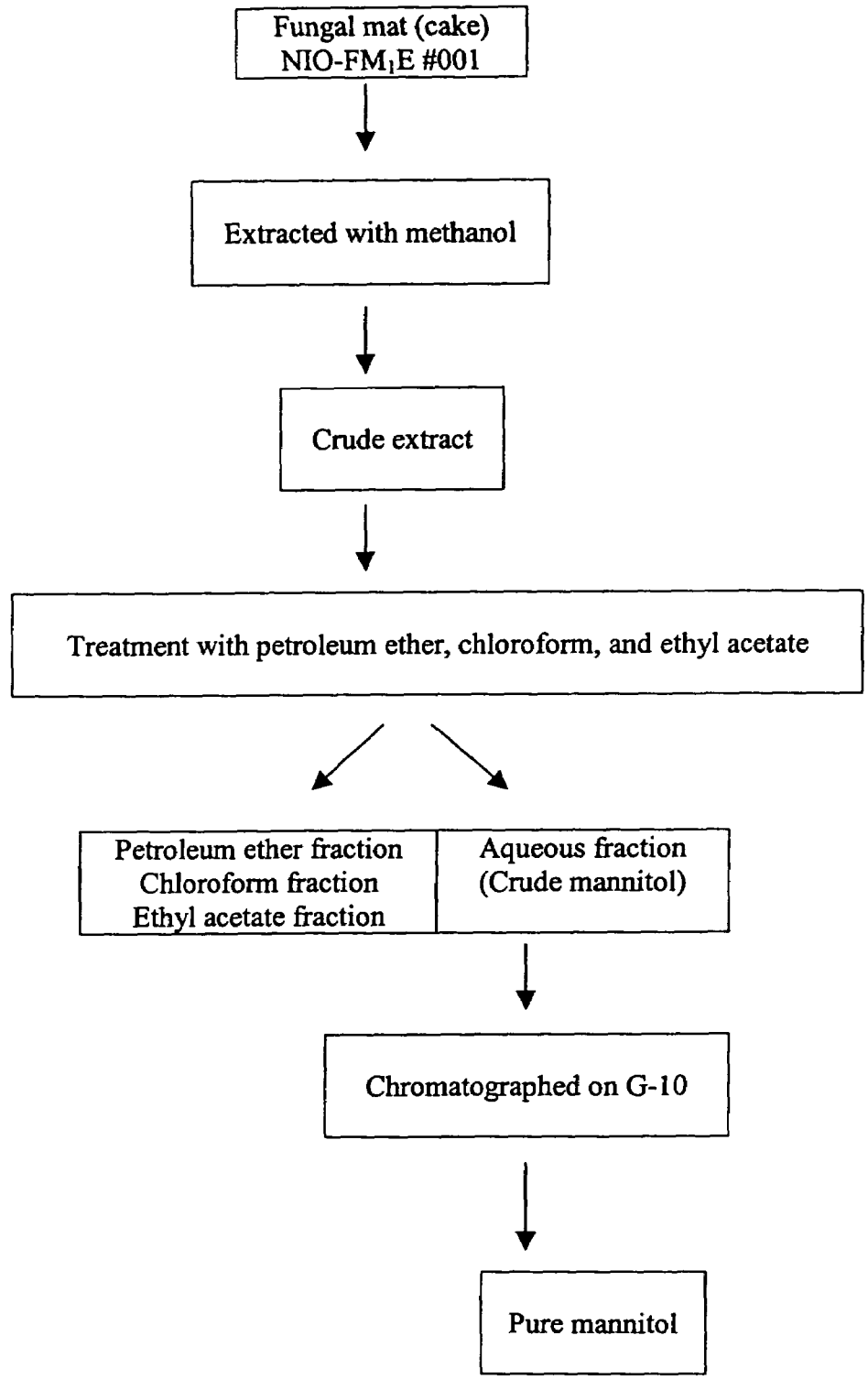

PLANT MANGROVE-ASSOCIATED FUNGUS *CURVULARIA LUNATA* AND A SIMPLE AND EFFICIENT METHOD OF OBTAINING HIGH YIELD OF PURE MANNITOL FROM THE SAME

This application is a divisional of U.S. application Ser. No. 10/464,845, filed Jun. 19, 2003, now abandoned the entire contents of which are incorporated herein by reference.

FIELD OF THE PRESENT INVENTION

The present invention relates to a plant mangrove-associated fungus *Curvularia lunata*, Strain FM1 E 001, of International deposition no. MTCC 5109, and a simple and efficient method of obtaining high yield of pure mannitol from a plant mangrove-associated fungus *Curvularia lunata*, said method comprising steps of cutting the leaves into small pieces and placing it on potato dextrose agar (PDA) plates for 48 hours, maintaining the culture at temperature ranging between 26-47° C. and salinity ranging between 4-32 ppt with occasional stress conditions for about 17-19 days to obtain mycelial mat, sonicating the mat to lyse the cells, extracting crude from the sonicated mat using methanol repeatedly, concentrating the crude, treating the concentrated crude extract with solvents of increasing polarity, obtaining aqueous fraction as white powder residue after the treatment containing crude mannitol, purifying the crude mannitol by chromatography to obtain pure mannitol with about 75% of the total crude extract.

BACKGROUND AND PRIOR ART REFERENCES OF THE PRESENT INVENTION

D-mannitol is a six-carbon sugar alcohol or polyol, which is about half as sweet as sucrose and occurs widely in nature in a variety of organisms including plants, algae, fungi, and certain bacteria. L-mannitol does not occur naturally.

Low levels of mannitol are found in several fruits and vegetables. Presently, mannitol is industrially produced by catalytic hydrogenation of fructose/glucose (1:1) mixture such as invert sugar. Raney-nickel is used as a catalyst and hydrogen gas is used at high temperature and pressure (Makkee et al., 1985). The disadvantage of this method is that the composition of the hydrogenated mixture consists of only about 25% mannitol and the remaining 75% was sorbitol. This production procedure makes the manufacture cost for mannitol relatively high.

Mannitol is known to have several applications both in plants and humans. Jennings (1984) stated that polyols including mannitol play several roles in fungi; as carbohydrate reserve, as translocatory compounds, as an osmoregulatory compound as in coenzyme regulation, storage or reducing power and has been also shown to quench reactive oxygen species (ROS). Reactive oxygen species are both signal molecules and direct participants in plant defense against pathogens. There is growing evidence that at least some phytopathogenic fungi use mannitol to suppress ROS mediated plant defenses (Jennings et al 1998).

Mannitol is a valuable nutritive sweetener because it is non-toxic, non-hygroscopic in its crystalline form and has no teeth decaying effects (Debord et al 1987; Dwivedi 1978). Mannitol does not induce hyperglycemia, which makes it useful for diabetics (Griffin and Lynch, 1972). It is used as a sweet builder in sugar free chewing gum and in pharmaceutical preparations (Soetaert, 1991).

The other uses of mannitol are that it is used for the treatment of ciguatera in Australia (Lewis, 1992). In emergency cases, mannitol is used in the treatment of head injury to decrease cerebral edema and intracranial pressure. Administration of mannitol in man induces diuresis (promotion of urinary excretion) in oligourea or forced diuresis in food poisoning cases. High doses of mannitol exert a laxative effect in man.

Several microorganisms are known to produce mannitol. Among bacteria, heterofermentative species belonging to the genera *Leuconostoc, Oenococcus*, and *Lactobacillus* seem to be most effective in producing mannitol (Niklas et al 2002). Several filamentous fungi (moulds) produce mannitol form glucose as well. Mannitol was earlier reported from fungal strains like *Aspergillus niger* (Muraleedharan, 1988), cotton dust associated fungi viz. *Alternaria alternata, Cladosporium herbarum, Epicoccum purpurascens* and *Fusarium pallidoroseum* (Domelsmith et al 1988), *Candida magnoliae* (Song et al 2002) and *Cephalosporium* sp. (Bi et al 2001).

The prior art biotechnical process for the conversion of sugar to mannitol has not proven entirely satisfactory, as they do not provide an adequate conversion yield and therefore the industrial production is still based on hydrogenation. Thus, there remains a need to improve the bioconversion of fructose and other substrate into mannitol in order to provide an industrially economical and acceptable process.

Our fungal culture, NIO-$FM_1$E#001 shows a considerable good yield (~70% of the total crude extract) and a relatively simple and economical process for the production of mannitol. Since mannitol has been reported to accumulate in response to environmental stress (Kets et al 1996; Stoop and Pharr, 1994), the fungus, NIO-$FM_1$E #001 was cultured under thermal and salt stress conditions to obtain maximum yield of polyol. Thus, our patent describes an economical process for the production of mannitol and a novel fungal source (NIO-$FM_1$E#001) for the production of the same.

OBJECTS OF THE PRESENT INVENTION

The main object of the present invention is to isolate a plant mangrove-associated fungus *Curvularia lunata* of International deposition no. . . . .

Another main object of the present invention is to isolate a fast growing fungus.

Yet another main object of the present invention is tom develop a simple and efficient method of obtaining high yield of pure mannitol from a plant mangrove-associated fungus *Curvularia lunata*.

Still another object of the present invention is to isolate a purified crude mannitol by chromatography to obtain pure mannitol with about 75% of the total crude extract. Still another object of the present invention is to isolate high percentage yield of mannitol using stress conditions.

Still another object of the present invention is to identify novel source for mannitol.

Still another object of the present invention is to identify novel strains of fungus which are easy to isolate and culture.

Still another object of the present invention is to use fermentation medium used for optimum yield is of low cost.

Still another object of the present invention is to develop a method of isolating mannitol, wherein secondary metabolites can be easily separated from the main compound.

Still another object of the present invention is to develop a method of isolating pure mannitol from fungi using room temperature and pressure and not catalyst is used for the production of mannitol.

SUMMARY OF THE PRESENT INVENTION

The present invention relates to a plant mangrove-associated fungus *Curvularia lunata*, Strain FM1 E 001, of International deposition no. MTCC 5109, deposited under the Budapest Treaty at the Microbial Type Culture Collection and Gene Bank, Institute of Microbial Technology, Sector 39-A, Chandigarh, 160 036, India on Jul. 4, 2003, and a simple and efficient method of obtaining high yield of pure mannitol from a plant mangrove-associated fungus *Curvularia lunata*, said method comprising steps of cutting the leaves into small pieces and placing it on potato dextrose agar (PDA) plates for 48 hours, maintaining the culture at temperature ranging between 26-47° C. and salinity ranging between 4-32 ppt with occasional stress conditions for about 17-19 days to obtain mycelial mat, sonicating the mat to lyse the cells, extracting crude from the sonicated mat using methanol repeatedly, concentrating the crude, treating the concentrated crude extract with solvents of increasing polarity, obtaining aqueous fraction as white powder residue after the treatment containing crude mannitol, purifying the crude mannitol by chromatography to obtain pure mannitol with about 75% of the total crude extract.

DETAILED DESCRIPTION OF THE PRESENT INVENTION

The present invention relates to a plant mangrove-associated fungus *Curvularia lunata*, Strain FM1 E 001, and a simple and efficient method of obtaining high yield of pure mannitol from a plant mangrove-associated fungus *Curvularia lunata*, said method comprising steps of cutting the leaves into small pieces and placing it on potato dextrose agar (PDA) plates for 48 hours, maintaining the culture at temperature ranging between 26-47° C. and salinity ranging between 4-32 ppt with occasional stress conditions for about 17-19 days to obtain mycelial mat, sonicating the mat to lyse the cells, extracting crude from the sonicated mat using methanol repeatedly, concentrating the crude, treating the concentrated crude extract with solvents of increasing polarity, obtaining aqueous fraction as white powder residue after the treatment containing crude mannitol, purifying the crude mannitol by chromatography to obtain pure mannitol with about 75% of the total crude extract.

In another embodiment of the present invention, wherein the fungus as claimed in claim 1, wherein the mangrove plant is *Acanthus illicifolius*.

In yet another embodiment of the present invention, wherein the fungus is fast growing fungus.

In still another embodiment of the present invention, wherein The fungus as claimed in claim 1, wherein the fungus is of color brown to blackish brown with black reverse.

In still another embodiment of the present invention, wherein The fungus as claimed in claim 1, wherein the fungus has conidia of pale brown color with three or more traverse septa and are formed apically through a pore (poroconidia) in a sympodially elongated geniculate conidiophore.

In still another embodiment of the present invention, wherein The fungus as claimed in claim 1, wherein the fungus shows conidia of cylindrical or slightly curve shape, with one of the central cells being larger and darker.

In still another embodiment of the present invention, wherein A simple and efficient method of obtaining high yield of pure mannitol from a plant mangrove-associated fungus *Curvularia lunata*, Strain FM1 E 001, said method comprising steps of:

obtaining leaves from the plant mangrove, rinsing the leaves in sterile seawater and keeping them in sterile, moist culture chamber for about two weeks, cutting the leaves into small pieces and placing it on potato dextrose agar (PDA) plates for 48 hours, transferring individual colonies aseptically into a sterile fresh PDA plate to obtain pure culture, maintaining the isolated fungal cultures on PDA slants for about 7 days to obtain mycelia, transferring the mycelia to a fresh PDB with seawater and distilled water using starch and sugar as source of carbon.

incubating the culture at temperature ranging between 26-32° C. for about 3-6 days to obtain inoculum, inoculating the PBD having seawater and distilled with the inoculum, maintaining the culture at temperature ranging between 26-47° C. and salinity ranging between 4-32 ppt with occasional stress conditions for about 17-19 days to obtain mycelial mat, sonicating the mat to lyse the cells, extracting crude from the sonicated mat using methanol repeatedly, concentrating the crude, treating the concentrated crude extract with solvents of increasing polarity, obtaining aqueous fraction as white powder residue after the treatment containing crude mannitol, purifying the crude mannitol by chromatography to obtain pure mannitol with about 75% of the total crude extract.

In still another embodiment of the present invention, wherein method as claimed in claim 7, wherein the plant is *Acanthus illicifolius*.

In still another embodiment of the present invention, wherein the starch is of concentration ranging between 3-5 g/l.

In still another embodiment of the present invention, wherein the dextrose is of the concentration ranging between 18-22 g/l.

In still another embodiment of the present invention, wherein the ratio of seawater and distilled water is ranging between 1:5 to 5:1, preferably 1:1.

In still another embodiment of the present invention, wherein the stress conditions is temperature ranging between 40-45° C.

In still another embodiment of the present invention, wherein the stress conditions is salinity ranging between 15-17 ppt.

In still another embodiment of the present invention, wherein the stress conditions lead to high percentage yield of mannitol.

In still another embodiment of the present invention, wherein the leaves are young, and living leaves.

In still another embodiment of the present invention, wherein concentrating the crude using vacuum evaporator at temperature ranging between 28-32° C.

In still another embodiment of the present invention, wherein the solvents in increasing polarity are petroleum ether, chloroform, and ethyl acetate.

In still another embodiment of the present invention, wherein the chromatography is on G-10 solid support.

The present invention relates to a mangrove-associated fungus NIO-FM₁E#001, as a novel source for the production of mannitol and a simple, economical, extraction and purification process for the production of the same. The fungal culture was isolated from living, young leaves of *Acanthus illicifolius*. The isolated culture was grown in potato dextrose broth containing potato starch and dextrose as carbon source, in sea water:distilled water (1:1). For optimum growth the fermentation medium was subjected to thermal and salt stress conditions. The polyol was obtained from mycelial mat involving minimum extraction and purification steps. The sugar was acetylated and its structure confirmed using spectroscopic techniques using, Mass Spectroscopy, high field NMR Spectroscopy, DEPT and COSY experiments.

A mangrove-associated fungus, *Curvularia lunata*, NIO-FM₁E#001, as a novel source for the production of mannitol and a simple, economical process for the extraction and purification of mannitol.

The fungus, NIO-FM₁E#001 was associated with a mangrove *Acanthus illicifolius*, and was isolated using the following steps.
   a. Fresh young leaves were collected in sterile polyethylene bags.
   b. The leaves were rinsed in sterile seawater and placed in sterile, moist, culture chamber for two weeks.
   c. The leaves were then cut with the help of sterile scalpel and the pieces were placed on sterile potato dextrose agar (PDA) plates.
   d. Individual colony was picked aseptically after 48 hours and transferred on to sterile PDA plates to obtain a pure culture.

The fungal innoculum was prepared by the following steps.
   a. The pure isolated fungal culture was maintained on PDA slants for 7 days.
   b. Plugs of agar supporting mycelial growth were cut aseptically and transferred into 100 ml Erlenmeyer flasks containing 25 ml potato dextrose broth (PDB).
   c. The medium uses potato starch (4 g/l) and dextrose (20 g/l) as carbon source.
   d. The fermentation broth was prepared in seawater: distilled water (1:1).
   e. Flasks were incubated between 28-30° C. on a rotor shaker for 4 to 5 days.

The innoculum used to seed the fermentation medium comprising of the following steps.
   a. Seed innoculum was poured aseptically into 5 liter Erlenmeyer flasks containing 1 liter PDB prepared in 1:1 seawater:distilled water.
   b. The temperature of the fermentation medium during innoculation was between 28-45° C.
   c. The incubation temperature of the fermentation medium was between 28-45° C.
   d. The salinity of the fermentation medium was between 5-30 ppt.
   e. The medium was kept under shaker conditions for 18 days.
   f. The temperature stress was given by maintaining the inoculation temperature of the fermentation medium between 40-45° C.
   g. In another preferred claim as claimed in claim 1, the incubation temperature of the fermentation medium was between 28-30° C.
   h. In yet another preferred claim as claimed in claim 1, salt stress was given by maintaining the salinity of the fermentation medium between 15-17 ppt.

The process as claimed in claim 1, the extraction involved the following steps.
   The dry mycelial mat was sonicated and repeatedly extracted using methanol.
   The crude from the extraction with organic solvent, was concentrated on a rotary vacuum evaporator at 30° C.
   The crude extract was treated with petroleum ether, chloroform and ethyl acetate to separate the petroleum ether fraction, chloroform fraction and ethyl acetate fraction.
   The aqueous fraction which remained as white powder contained crude polyol (~70% of the total crude extract).

NMR spectra of the crude aqueous extract showed the polyol to be mannitol. Acetylation of mannitol gave hexacetate of the polyol, which was further used for its confirmation.

The crude mannitol was chromatographed on G-10 solid support for purification.

In a preferred claim as claimed in claim 1, the solvent system used was methanol:water (95:5).

BRIEF DESCRIPTION OF THE ACCOMPANYING DRAWINGS

FIG. 1 shows the flow diagram for the extraction and purification of mannitol. Accordingly, the present invention describes a mangrove-associated fungus, *Curvularia lunata*, NIO-FM₁E#001 as a novel source for the production of mannitol and a simple and economical process for the extraction and purification of the same.

In an embodiment of the present invention, the fungus used for the production of mannitol was associated with young leaves of mangrove, *Acanthus illicifolius* and isolated by the following steps.
   Fresh, young leaves were collected in sterile polyethylene bags.
   They were rinsed in sterile seawater and placed in a sterile, moist, culture chamber for two weeks.
   The leaves were cut using sterile scalpel and transferred aseptically into PDA (potato dextrose agar) plates (Hi-Media Laboratories Ltd.).
   After 48 hours the fungal colony was removed and again placed on PDA plates till pure isolates of the culture was obtained.

In another embodiment of the present invention, the innoculum for the fungal culture was prepared by the following steps.
   Initially the culture was grown on PDA slants for 7 days.
   Plugs of agar supporting the mycelial growth was cut aseptically and transferred into 100 ml Erlenmeyer flasks containing 25 ml PDB (potato dextrose broth).
   The medium was prepared in seawater:distilled water (1:1).
   Potato starch (4 g/l) and dextrose (20 g/l) were used as carbon source.
   Flasks were incubated on a rotor shaker between 28-30° C. for 4 to 5 days.

In yet another embodiment of the present invention, the above innoculum was used to seed 5 liter Erlenmeyer flasks containing 1 liter of potato dextrose broth prepared in 1:1 seawater: distilled water.
   The fermentation medium during innoculation process was between 28-45° C.

After inoculation the fermentation medium was placed on a shaker for 18 days between 28-45° C.

The salinity of the medium used was between 5-30 ppt.

In still another preferred embodiment of the present invention, temperature stress was given by maintaining the fermentation medium during inoculation between 40-45° C.

In still another preferred embodiment of the present invention, the incubation temperature of the fermentation medium was maintained between 28-30° C.

In yet another preferred embodiment of the present invention, salt stress was provided to the culture by maintaining the salinity of the fermentation medium between 15-17 ppt.

In still another embodiment, fungal mycelia were recovered by filtration, dried in a lyophilizer and extracted repeatedly with methanol after sonication for cell lysis. The crude from the extraction with organic solvent was concentrated on a rotor vacuum evaporator at 30° C. The crude extract was treated with petroleum ether to remove the petroleum ether fraction, treated with chloroform to remove the chloroform fraction and finally treated with ethyl acetate to remove the ethyl acetate fraction. The aqueous fraction left behind in the flask contained a crude white powder, which constituted about 70% of the total crude extract.

In a further embodiment of the present invention, NMR of this white powder showed it to contain a polyol and comparison of the NMR spectral data with standards showed the polyol to be mannitol. Mannitol was acetylated using pyridine and acetic anhydride to yield hexacetate, whose spectral values further confirm the presence of mannitol.

In still another embodiment of this invention, crude mannitol was chromatographed on G-10 solid support for purification.

In a preferred embodiment of the present invention, the mobile phase used comprised of methanol:water (95:5) to obtain pure mannitol.

The invention is further described in detail with the help of the following examples and should not be construed to limit the scope of this invention.

EXAMPLE-1

The leaves from the mangrove plant, *Acanthus illicifolius* was collected from Sinquerim, Goa coast, India. This fungal culture inhabit *Acanthus illicifolius* without causing apparent harm to the host. This fungus was isolated from healthy, young leaves where symptoms of fungal infection could not be detected.

After collection of fresh young leaves of *Acanthus*, they were transferred to the laboratory in sterile polyethylene bags. The leaves were rinsed with sterile filtered seawater to remove adhered particles and detritus material. The leaves were next kept in a sterile culture chamber for two weeks. At the end of two weeks, the leaves were cut with the help of a sterile scalpel and the pieces were placed on PDA plates. Individual colony was picked aseptically and transferred repeatedly on PDA plates to obtain a pure culture.

EXAMPLE-2

The isolated culture was designated as *Curvularia lunata*, NIO-FM$_1$E#001. Colonies of NIO-FM$_1$E #001 are fast growing, brown to blackish brown with a black reverse. Conidia are pale brown with three or more traverse septa and are formed apically through a pore (poroconidia) in a sympodially elongated geniculate conidiophore. Conidia are cylindrical or slightly curved, with one of the central cells being larger and darker.

The purified culture was grown on PDA slants for 7 days. Plugs of agar supporting mycelial growth were cut and transferred aseptically to a 100 ml Erlenmeyer flask containing 25 ml potato dextrose broth (HiMedia Laboratories Ltd.) prepared in seawater:distilled water (1:1). The carbon source in this broth was potato starch 4 g/l and dextrose 20 g/l. Flasks were kept under shaker conditions between 28-30° C. for 4-5 days. Subculture from the above flask was aseptically transferred to 5 liter flasks containing 1 liter of the above-mentioned medium. The innoculation was carried out by keeping the temperature of the fermentation medium between 40-45° C. After innoculation, the flasks were kept under shaker conditions for 18 days between 28-30° C.

EXAMPLE-3

At the end of the incubation period, mycelia were recovered by filtration and dried in a lyophilizer to determine biomass weight. Dry fungal mat (cake) was extracted with methanol several times with repeated sonication of the cake for cell lysis. The filtrate thus obtained was concentrated to free it from the organic solvent under vacuum evaporation. This resulted in the crude extract of the sample. The crude extract was treated successively with solvents of increasing polarity like petroleum ether, chloroform and ethyl acetate to separate the petroleum ether fraction, chloroform fraction, and ethyl acetate fraction respectively. The last aqueous fraction contained the sugar alcohol as white powder, which constituted about 70% of the total crude extract.

EXAMPLE-4

The white crude powder was chromatographed on G-10 solid support using methanol: water (95:5%) as eluent, to free it from any possible salt contamination. The pure mannitol thus obtained was identified by comparison of its NMR data with spectra reported in Aldrich Catalogue, Vol. 1, pp 289c.

EXAMPLE-5

A subfraction of the above mannitol was acetylated to obtain the acetyl derivative of the polyol and structure was further confirmed by various spectroscopic methods. For acetylation, mannitol (30 mg) was dissolved in pyridine (2 ml), to which a solution of 3 ml acetic anhydride in pyridine was added and left overnight. The mixture was taken in chloroform and pyridine was removed by washing with dilute HCl. This was followed by washing with distilled water. Chloroform was evaporated and the residue was chromatographed over silica gel to yield 35 mg of mannitol hexaacetate whose structure was confirmed by spectroscopic methods and comparison of spectra with the reported spectral data (Fairbanks and Sinay, 1995).

Advantages of the Present Invention

1. This is a novel source for mannitol.
2. It is a common fungus (found associated with mangrove leaves of *Acanthus illicifolius*, collected from Goa coast).
3. Easy to isolate and culture.
4. The fermentation medium used for optimum yield is of low cost.
5. The fermentation conditions are feasible and can be easily carried out in the laboratory.
6. The secondary metabolites can be easily separated from the main compound.

7. Can be preserved using standard techniques and revived as and when required.
8. The extraction process of mannitol from fungal mat and purification of the same involves simple techniques as compared to the commercial preparation of mannitol.
9. We used room temperature and pressure and no catalyst is used for the production of mannitol. Commercially, mannitol is still produced by the catalytic hydrogenation of a 50:50 fructose:glucose mixture which uses hydrogen at high temperature and pressure with Raney Nickel as a catalyst.
10. We produced good yield of mannitol (~70% of crude extract) without any other polyol contamination. Commercially, hydrogenation of fructose syrups or invert sugar resulted in the coproduction of another sugar alcohol, sorbitol and the yield of mannitol is only 25%.
11. In the present invention, the crude mannitol was chromatographed using G-10 as solid support, using methanol:water (95:5) as eluent for final purification.

On the other hand, the purification steps in the commercial production of mannitol are tedious.

REFERENCES

Bi Y., Wang H., Chen Y., Xie J., (2001). Studies on chemical constituents of mycelium of fungus *Cephalosporium* sp. AL031 (1). Journal of Chinese Medicinal Materials. Vol. 24(8), 568-569.

Debord B., Lefebvre C., Guyot-Hermann A. M., Hubert J., Bouche R., and Guyot J. C. (1987). Study of different forms of mannitol: Comparative behaviour under compression. Drug Development and Industrial Pharmacy, 13, 1533-1546.

Domelsmith L. N., Klich M. A., Goynes W. R., (1988). Production of mannitol by fungi form cotton dust. Applied and Environmental Microbiology. Vol. 54(7), 1784-1790.

Dwivedi B. K., (1978). Low calorie and special dietary foods. West Palm Beach: CRC Press, Inc.

Fairbanks A. J. and Sinay P., (1995). Synthesis of a peracetylated stereoisomer of De Rosa's Calditol: Some Questions about the Corrections of the Original Structure Assigned to this Natural Product. Tetrahedron Letters, Vol. 36(6), 893-896.

Griffin W. C. and Lynch M. J., (1972). Polyhydric alcohol. In T. E., Furia (ed) CRC Handbook of food additives. Vol. 1 ($2^{nd}$ ed) (pp 431-455). Cleveland, Ohio: CRC Press Inc.

Jennings D. H., (1984). Polyol metabolism in fungi. Advances in Microbial Physiology, 25, 149-193.

Jennings D. B., Ehrenshaft M; Pharr D. M., Williamson J. D., (1998). Proceedings of the National Academy of Science of the United States of America. Vol. 95(25), 15129-15133.

Kets E. P. W., De Bont J. A. M., and Heipieper H. J. (1996). Physiological response of *Pseudomonas putida* S., 12 subjected to reduced water activity. FEMS Microbiology Letters, 139, 133-137.

Lewis R. J., Mannitol: The treatment of choice in the acute phase of ciguatera; Ciguatera Inf. Bull., (1992), 2, 9-10.

Makkee M., Kieboom A. P. G., and Van Bekkum H., (1985). Production methods of D-mannitol. Starch, 37, 136-141.

Muraleedharan G. Nair and Basil A. Burke. (1988). A new fatty and methyl ester and other biologically active compound from *Aspergillus niger*. Phytochemistry. Vol. 27(10), 3169-3173.

Niklas Von Weymarn, Mervi Hujanen and Matti Leisola (2002) Production of D-mannitol by heterofermentative lactic acid bacteria. Process Biochemistry. 37, 1207-1213.

Soetaert W., (1991). Synthesis of D-mannitol and L-sorbose by microbial hydrogenation and dehydrogenation of monosaccharides. Ph.D. Thesis, University of Gent, Gent, Belgium.

Song K. H., Lee J. K., Song J. Y., Hong S. G., Baek H., Kim S. Y., Hyun H. H., (2002). Production of mannitol by a novel strain of *Candida magnoliae*. Biotechnology letters Vol. 24(1), 9-12.

Stoop J. M. H., and Pharr B. M., (1994). Mannitol metabolism in celery stressed by excess macronutrients. Plant Physiology, 106, 503-511.

Yun J. W., and Kang S. C and Song S. K. (1996). Microbial transformation of fructose to mannitol by *Lactobacillus* sp. KY-107. Biotechnology Letters. 18, 35-40.

The invention claimed is:

1. A simple and efficient method of obtaining high yield of pure mannitol from a plant mangrove-associated fungus *Curvularia lunata* of International deposition No. MTCC 5109, said method comprising steps of:
   a. obtaining leaves from the plant mangrove,
   b. rinsing the leaves in sterile seawater and keeping them in sterile, moist culture chamber for about two weeks,
   c. cutting the leaves into small pieces and placing it on potato dextrose agar (PDA) plates for about 48 hours,
   d. transferring individual colonies aseptically into a sterile fresh PDA plate to obtain pure culture,
   e. maintaining the isolated fungal cultures on Potato Dextrose Agar (PDA) slants for about 7 days to obtain mycelia,
   f. transferring the mycelia to a fresh Potato Dextrose Broth (PDB) medium with seawater and distilled water using starch and sugar as source of carbon,
   g. incubating the culture at temperature ranging between 26-32° C. for about 3-6 days to obtain inoculum,
   h. inoculating the PDB medium having seawater and distilled water with the inoculum,
   i. maintaining the culture at temperature ranging between 26-47° C. and salinity ranging between 4-32 ppt with occasional stress conditions for about 17-19 days to obtain mycelial mat,
   j. sonicating the mat to lyse the cells,
   k. extracting crude from the sonicated mat using methanol repeatedly,
   l. concentrating the crude,
   m. treating the concentrated crude extract with solvents of increasing polarity,
   n. obtaining aqueous fraction as white powder residue after the treatment containing crude mannitol,
   o. purifying the crude mannitol by chromatography to obtain pure mannitol with about 75% of the total crude extract.

2. A method as claimed in claim 1, wherein the plant is *Acanthus illicifolius*.

3. A method as claimed in claim 1, wherein the starch is of concentration ranging between 3-5 g/l.

4. A method as claimed in claim 1, wherein the dextrose is of the concentration ranging between 18-22 g/l.

5. A method as claimed in claim 1, wherein the ratio of seawater and distilled water is 1:1.

6. A method as claimed in claim 1, wherein the stress conditions are temperature ranging between 40-45° C.

7. A method as claimed in claim 1, wherein the stress conditions are salinity ranging between 15-17 ppt.

8. A method as claimed in claim 1, wherein the stress conditions lead to high percentage yield of mannitol.

9. A method as claimed in claim 1, wherein the leaves are young, and living leaves.

10. A method as claimed in claim 1, wherein concentrating the crude comprises using vacuum evaporator at temperature ranging between 28-32° C.

11. A method as claimed in claim 1, wherein the solvents in increasing polarity are petroleum ether, chloroform, and ethyl acetate.

12. A method as claimed in claim 1, wherein the chromatography is on G-10 solid support.

* * * * *